US005675057A

United States Patent [19]

Bremer et al.

[11] Patent Number: 5,675,057
[45] Date of Patent: Oct. 7, 1997

[54] METHOD OF IMPROVING CATALYST ACTIVITY, IMPROVED CATALYSTS AND THEIR USE

[75] Inventors: Noel L. Bremer, Kent; Linda C. Brazdil; James F. Brazdil, both of Highland Hts.; Fernando A. P. Cavalcanti, South Euclid, all of Ohio

[73] Assignee: BP America Inc., Cleveland, Ohio

[21] Appl. No.: 476,362

[22] Filed: Jun. 7, 1995

Related U.S. Application Data

[62] Division of Ser. No. 112,027, Aug. 26, 1993, abandoned.

[51] Int. Cl.[6] .................. C07C 253/24; B01J 23/14; B01J 23/16; B01J 23/18
[52] U.S. Cl. .................. 558/319; 558/327; 546/286; 502/338; 502/325; 502/350; 502/352; 502/202; 502/215; 502/310
[58] Field of Search .................. 558/319, 327; 546/286

[56] References Cited

U.S. PATENT DOCUMENTS

| | | | |
|---|---|---|---|
| 4,336,205 | 6/1982 | Onishi et al. | 558/327 |
| 4,388,248 | 6/1983 | Wise | 558/325 |
| 4,447,558 | 5/1984 | Sasaki et al. | 502/215 |
| 4,524,236 | 6/1985 | McCain | 585/658 |
| 4,558,028 | 12/1985 | Tsuneki et al. | 502/211 |
| 4,784,979 | 11/1988 | Toft et al. | 502/8 |
| 4,849,391 | 7/1989 | Riva et al. | 502/202 |
| 4,939,260 | 7/1990 | Inoue et al. | 546/286 |
| 5,008,427 | 4/1991 | Brazdil, Jr. et al. | 558/319 |
| 5,094,989 | 3/1992 | Lynch et al. | 502/202 |
| 5,214,016 | 5/1993 | Brazdil et al. | 502/202 |
| 5,258,543 | 11/1993 | Suresh et al. | 558/325 |

*Primary Examiner*—Alan L. Rotman
*Attorney, Agent, or Firm*—Michael F. Esposito; David J. Untener

[57] ABSTRACT

Disclosed is a process comprising the heat treatment of certain V and Sb-containing catalysts at a lower temperature than the previous calcination temperature of the base catalyst to improve catalytic performance; the catalysts resulting from such process; and certain oxidation and ammoxidation reactions in the presence of such a catalyst.

11 Claims, No Drawings

5,675,057

METHOD OF IMPROVING CATALYST ACTIVITY, IMPROVED CATALYSTS AND THEIR USE

This is a divisional application of application Ser. No. 08/112,027, filed Aug. 26, 1993, now abandoned.

This invention in one aspect relates to a method of making an improved catalyst and to the catalyst so made. In another aspect the invention relates to the oxidation and atomoxidation of paraffins, olefins and aromatic compounds.

Catalysts containing vanadium and antimony in oxide form, and usually containing tin or titanium, or both, as part of the metal oxide catalyst are normally calcined before using to catalyze the atomoxidation of paraffins, olefins and various aromatics; such calcination is above 750° C. and activates the composition to make effective atomoxidation catalysts.

It has now been found that such catalysts can be even further activated to increase the activity of conversion of the feedstock and the selectivity of conversion to a nitrile by the heat treatment of the catalyst previously activated by calcining at a temperature above 750° C., wherein the heat treatment is at an effective temperature at least 50° C. below the highest calcination temperature.

In a broad aspect of the method of the invention we have found that heat treating a catalyst calcined at a calcining temperature above 750° C. at a temperature which is at least 500° C. and at least 50° C. below the calcining temperature is improved in its activity for converting the feed, such as propane or propylene to acrylonitrile.

In a now preferred embodiment of the method for making an even more active catalyst, the catalyst which has been calcined at a temperature above 750° C. and thereafter heat treated at the lower temperature, is contacted with a liquid believed to be a solvent for some minute quantity of a deleterious (generally well less than 1% of the composition) compound containing V and Sb in oxide form, and the bulk of the "solvent" separated, from the catalyst.

In this aspect of the invention there can be used various "solvents" that have been used to so treat such V and Sb catalysts in oxide form following calcination above 750° C. These include water, aqueous solutions of acids or bases, such as phosphoric, sulfuric and acetic acids and $NH_3$ and NaOH solutions; and the hydroxy compounds of U.S. Pat. No. 5,094,989: cyclohexanol; cyclopentanol; a monohydroxy, acyclic hydrocarbon having 1–8 C atoms; and a dihydroxy, acyclic hydrocarbon having 2–4 carbon atoms.

The catalyst to which the improved method applies contains the elements and relative amounts indicated by the formula:

$$V_vSb_mA_aD_dO_x$$

wherein

A when present is Sn and/or Ti;

D when present is one or more of Li, Mg, Na, Ca, Sr, Ba, Co, Fe, Cr, Ca, Ni, Zn, Ge, Nb, Zr, Mo, W, Cu, Te, Ta, Se, Bi, Ce, In, As, B, Al and Mn;

and wherein all of the elements of said formula except oxygen are present as cations, and v is 1 m is 0.5–10 a is up to 10 d is up to 10 x is determined by the oxidation state of the cations present

In a more specific aspect of the invention the catalyst to which the method applies has the relation

The process for improving the catalysts is most often applied to such foregoing catalysts wherein a is ≦v+m.

In the above formula the phrase "when present" means that A may be zero and that D may be zero. Thus, the catalysts can contain essentially only V and Sb.

The highest calcination temperature of the catalysts above 750° C. before the relatively low temperature heat treatment step of the process of the invention can be as high as 1200° C., but is usually over 750° C. and up to 1050° C., most often up to 950° C.

The present catalyst is useful for the oxidation and ammoxidation of paraffins, olefins and aromatic compounds in a reaction zone. In particular, in this aspect of the invention especially useful reactions include the ammoxidation of propane with $NH_3$ and $O_2$ to acrylonitrile, the ammoxidation of propylene with $NH_3$ and $O_2$ to acrylonitrile, the atomoxidation of a methyl pyridine with $O_2$ and $NH_3$ to the corresponding cyanopyridine, and the atomoxidation of m-xylene with $O_2$ and $NH_3$ to isophthalonitrile.

The following specific examples are illustrative only and are not to be considered in any way limiting.

CATALYST EXAMPLE 1

27.42 g of $V_2O_5$ powder was added to a solution consisting of 100 ml of 30% $H_2O_2$ in 900 ml of water in a 2 liter beaker. After the reaction of the $V_2O_5$ powder was complete, 61.22 g of $Sb_2O_3$ and 2.40 g of fumed $TiO_2$ (Degussa P-25) powder were added. The beaker was covered with a watch glass and the mixture was stirred and heated for about 3 hours. 89.52 g of 10.1% $SnO_2$ sol (Nalco Chemical Co.) was added to the foregoing dispersion. The mixture was stirred in an uncovered beaker with heating in order to reduce the volume to 300 ml by evaporation of water. It was then dried in an oven at 120° C. Thereafter it was calcined for 8 hours at 650° C., cooled and then crushed and sieved to 20–35 mesh. A portion of this catalyst was calcined for 3 hours at 810° C. It was then contacted with isobutanol using about 6.25 ml of isobutanol per gram of catalyst by placing the catalyst in a coarse glass frit funnel, pouring the isobutanol over the catalyst, stiffing the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst. The catalyst was then heat treated in an oven at 500° C. for 3 hours according to the invention.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, and then allowing the isobutanol to pass through the funnel without suction. This was done a total of two times. After the last of the isobutanol had passed through the funnel, the catalyst was heated in an oven at 120° C. to remove the residual isobutanol on the catalyst.

The catalyst was used to atomoxidize propane using a ⅛ inch O.D. titanium metal fixed bed reactor equipped with a preheat leg and immersed in a temperature controlled molten salt bath. 4.0 g of catalyst were placed in the reactor. Results of all atomoxidation runs are shown in Tables 1 and 2 as are the feed ratios and temperatures.

CATALYST EXAMPLE 2

27.42 g of $V_2O_5$ powder was added to a solution consisting of 100 ml of 30% $H_2O_2$ in 900 ml of water in a 2 liter beaker. After the reaction of the $V_2O_5$ powder was complete, 61.22 g of $Sb_2O_3$, 2.4 g of fumed $TiO_2$ (Degussa P-25) power were added. The beaker was covered with a watch glass and the mixture was stirred and heated for about 3 hours. 89.52 g of 10.1% $SnO_2$ sol (Nalco Chemical Co.) was added to the foregoing dispersion. The mixture was stirred in an uncovered beaker with heating in order to reduce the volume to 300 ml by evaporation of water. It was then dried in an oven at 120° C. Thereafter it was calcined for 8 hours at 650° C., cooled and then crushed and sieved to 20–35 mesh. A portion of this catalyst was calcined for 3 hours at 810° C. It was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst. The catalyst was then heat treated in an oven at 650° C. for 3 hours according to the invention.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, and then allowing the isobutanol to pass through the funnel without suction. This was done a total of two times. After the last of the isobutanol had passed through the funnel, the catalyst was heated in an oven at 120° C. to remove the residual isobutanol on the catalyst.

The catalyst was used to atomoxidize propane using a ⅛ inch O.D. titanium metal fixed bed reactor equipped with a preheat leg and immersed in a temperature controlled molten salt bath. 4.0 g of catalyst were placed in the reactor.

CATALYST EXAMPLE 3

27.42 g of $V_2O_2$ powder was added to a solution consisting of 100 ml of 30% $H_2O_2$ in 900 ml of water in a 2 liter beaker. After the reaction of the $V_2O_5$ powder was complete, 61.22 g of $Sb_2O_3$, 2.4 g of fumed $TiO_2$ (Degussa P-25) powder were added. The beaker was covered with a watch glass and the mixture was stirred and heated for about 3 hours. 89.52 g of 10.1% $SnO_2$ sol (Nalco Chemical Co.) was added to the foregoing dispersion. The mixture was stirred in an uncovered beaker with heating in order to reduce the volume to 300 ml by evaporation of water. It was then dried in an oven at 120° C. Thereafter it was calcined for 8 hours at 650° C., cooled and then crushed and sieved to 20–35 mesh. A portion of this catalyst was calcined for 3 hours at 810° C. It was then contacted with isobutanol using,about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst. The catalyst was then heat treated in an oven at 650° C. for 3 hours according to the invention.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, and then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to ammoxidize propane using a ⅛ inch O.D. titanium metal fixed bed reactor equipped with a preheat leg and immersed in a temperature controlled molten salt bath. 4.5 g of catalyst were placed in the reactor.

Comparative Catalyst Example A 27.42 g of $V_2O_5$ powder was added to a solution consisting of 100 ml of 30% $H_2O_2$ in 900 ml of water in a 2 liter beaker. After the reaction of the $V_2O_5$ powder was complete, 61.22 g of $Sb_2O_3$ and 2.40 g of fumed $TiO_2$ (Degussa P-25) powder were added. The beaker was covered with a watch glass and the mixture was stiffed and heated for about 3 hours. 89.52 g of 10.1% $SnO_2$ sol (Nalco Chemical Co.) was added to the foregoing dispersion. The mixture was stiffed in an uncovered beaker with heating in order to reduce the volume to 300 ml by evaporation of water. It was then dried in an oven at 120° C. Thereafter it was calcined for 8 hours at 650° C., cooled and then crushed and sieved to 20–35 mesh. A portion of this catalyst was calcined for 3 hours at 810° C.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to atomoxidize propane using a ⅛ inch O.D. titanium metal fixed bed reactor equipped with a preheat leg and immersed in a temperature controlled molten salt bath. 2.5 g of catalyst were placed in the reactor. Results are summarized in Table 1.

CATALYST EXAMPLE 4

27.44 g $V_2O_5$ was added to a solution consisting of 100 ml 30% $H_2O_2$ in 900 ml of water in a 2 liter beaker. The mixture was stirred without heating for about 6 hours to produce a deep red sol/gel. It was then stirred overnight at room temperature. 61.26 g $Sb_2O_3$ was then added and the resulting mixture was heated to boiling and allowed to boil with a watch glass covering the beaker for about 3 hours. Water was periodically added to the beaker to keep the mixture stirring and the volume of the mixture constant. During the heating the mixture turned green then gray then gray-black. At this point 84.56 g of a 10.7 weight percent tin oxide sol and 2.4 g of $TiO_2$ were added and the mixture was evaporated to near dryness on the hot plate with constant stirring. The resulting paste was then dried at 120° C. overnight. The dried material was heat treated at 650° C. for 8 hours then ground and screened and the 20–35 mesh particles were collected. A portion of the 20–35 mesh particles was heat treated at 810° C. for 3 hours. A portion of the 810° C. calcined particles was washed three times with isobutanol by using about 50 ml of isobutanol per 8 grams of catalyst. The particles were placed in a coarse glass frit funnel, covered with isobutanol and the isobutanol was allowed to pass through the glass frit without suction. The resulting material was then placed in an oven at 120° C. for several hours to remove residual isobutanol. The composition was then heat treated for 3 hours at 650° C. and washed and heated as in Catalyst Example 3. As will be seen by reference to Table 1, an improvement was effected in yield and selectivity by the later 650° C. heat treatment, compared to Comparative Catalyst Example B.

Comparative Catalyst Example B 27.44 g $V_2O_5$ was added to a solution consisting of 100 ml 30% $H_2O_2$ in 900 ml of water in a 2 liter beaker. The mixture was stirred without heating for about 6 hours to produce a deep red sol/gel. It was then stiffed overnight at room temperature. 61.26 g $Sb_2O_3$ was then added and the resulting mixture was heated to boiling and allowed to boil with a watch glass covering the beaker for about 3 hours. Water was periodically added to the beaker to keep the mixture stirring and the volume of the mixture constant. During the heating the mixture turned green then gray then gray-black. At this point 84.56 g of a 10.7 weight percent tin oxide sol and 2.4 g of $TiO_2$ were added and the mixture was evaporated to near dryness on the hot plate with constant stirring. The resulting paste was then dried at 120° C. overnight. The dried material was heat treated at 650° C. for 8 hours then ground and screened and the 20–35 mesh particles were collected. A portion of the 20–35 mesh particles was heat treated at 810° C. for 3 hours. A portion of the 810° C. calcined particles was washed three times with isobutanol by using about 50 ml of isobutanol per 8 grams of catalyst. The particles were placed in a coarse glass frit funnel, covered with isobutanol and the isobutanol was allowed to pass through the glass frit without suction. This was done three times. The resulting material was then placed in an oven at 120° C. for several hours to remove residual isobutanol.

CATALYST EXAMPLE 5

27.44 g $V_2O_5$ was added to a solution consisting of 100 ml 30% $H_2O_2$ in 900 ml of water in a 2 liter beaker. The mixture was stirred without heating for about 6 hours to produce a deep red sol/gel. It was then stirred overnight at room temperature. 61.26 g $Sb_2O_3$ was then added and the resulting mixture was heated to boiling and allowed to boil with a watch glass covering the beaker for about 3 hours. Water was periodically added to the beaker to keep the mixture stirring and the volume of the mixture constant. During the heating the mixture turned green, then gray then gray-black. At this point 84.56 g of a 10.7 weight percent tin oxide sol and 2.4 g of $TiO_2$ were added and the mixture was evaporated to near dryness on the hot plate with constant stirring. The resulting paste was then dried at 120° C. overnight. The dried material was heat treated at 650° C. for 8 hours then ground and screened and the 20–35 mesh particles were collected. A portion of the 20–35 mesh particles was heat treated at 810° C. for 3 hours. A portion of the 810° C. calcined particles was heat treated according to the invention for 3 hours at 650° C. and was washed with isobutanol by using about 50 ml of isobutanol per 8 grams of catalyst. The particles were placed in a coarse glass frit funnel, covered with isobutanol and the isobutanol was allowed to pass through the glass frit without suction. This was done a total of three times. The resulting material was then placed in an oven at 120° C. for several hours to remove residual isobutanol.

It will be seen by reference to Table 1 that the post heat treatment for 3 hours at 650° C. was an improvement in comparison to both comparative catalyst examples B and C.

Comparative Catalyst Example C 27.44 g $V_2O_5$ was added to a solution consisting of 100 ml 30% $H_2O_2$ in 900 ml of water in a 2 liter beaker. The mixture was stirred without heating for about 6 hours to produce a deep red sol/gel. It was then stirred overnight at room temperature. 61.26 g $Sb_2O_3$ was then added and the resulting mixture was heated to boiling and allowed to boil with a watch glass covering the beaker for about 3 hours. Water was periodically added to the beaker to keep the mixture stirring and the volume of the mixture constant. During the heating the mixture turned green then gray then gray-black. At this point 84.56 g of a 10.7 weight percent tin oxide sol and 2.4 g of $TiO_2$ were added and the mixture was evaporated to near dryness on the hot plate with constant stirring. The resulting paste was then dried at 120° C. overnight. The dried material was heat treated at 650° C. for 8 hours then ground and screened and the 20–35 mesh particles were collected. A portion of the 20–35 mesh particles was calcined at 810° C. for 3 hours. This was designated Comparative Catalyst Example C. Results of testing this catalyst in the atomoxidation of propane are shown in Table 1.

CATALYST EXAMPLE 6

27.44 g $V_2O_5$ was added to a solution consisting of 100 ml 30% $H_2O_2$ in 900 ml of water in a 2 liter beaker. The mixture was stirred without heating for about 6 hours to produce a deep red sol/gel. It was then stirred overnight at room temperature. 61.26 g $Sb_2O_3$ was then added and the resulting mixture was heated to boiling and allowed to boil with a watch glass covering the beaker for about 3 hours. Water was periodically added to the beaker to keep the mixture stirring and the volume of the mixture constant. During the heating the mixture turned green then gray then gray-black. At this point 84.56 g of a 10.7 weight percent tin oxide sol and 2.4 g of $TiO_2$ were added and the mixture was evaporated to near dryness on the hot plate with constant stirring. The resulting paste was then dried at 120° C. overnight. The dried material was heat treated at 650° C. for 8 hours then ground and screened and the 20–35 mesh particles were collected. A portion of the 20–35 mesh particles was calcined at 810° C. for 3 hours and then heat treated according to the invention at 650° C. for 3 hours. As will be seen in Table 1,there is an improvement in the yield and selectivity in the atomoxidation of propane brought about by the final lower temperature heat treatment at 650° C. Compare the results with the results when using Comparative Catalyst Example C.

CATALYST EXAMPLE 7

27.44 g $V_2O_5$ powder was added to a solution consisting of 100 ml 30% $H_2O_2$ in 900 ml of water in a 2 liter beaker. After the reaction of the $V_2O_5$ powder was complete, 61.26 g of $Sb_2O_3$ was added. The beaker was covered with a watch glass and the mixture was stirred and heated for about 3 hours. 84.56 g of 10.7% SnO₂ sol (Nalco Chemical Co.) and 2.40 g of TiO₂ powder were added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C. then heat treated at 650° C. for an additional 3 hours.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to atomoxidize propane using a ⅛ inch O.D. titanium metal fixed bed reactor equipped with a preheat leg and immersed in a temperature controlled molten salt bath. 8.14 g of catalyst were placed in the reactor. Results are summarized in Table 1.

CATALYST EXAMPLE 8

27.29 g V₂O₅ powder was added to a solution consisting of 100 ml 30% H₂O₂ in 900 ml of water in a 2 liter beaker. After the reaction of the V₂O₅ powder was complete, 56.85 g of Sb₂O₃ was added. The beaker was covered with a watch glass and the mixture was stirred and heated for about 3 hours. 42.25 g of 10.7% SnO₂ sol (Nalco Chemical Co.) and 2.40 g of TiO₂ powder were added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C. then at 650° C. for an additional 3 hours.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was, done a total of three times. After the last of the isobutanol had passed through the funnel, the catalyst was heated in an oven at 120° C. to remove the residual isobutanol on the catalyst.

The catalyst was used to atomoxidize propane using a ⅛ inch O.D. titanium metal fixed bed reactor equipped with a preheat leg and immersed in a temperature controlled molten salt bath. 8.285 g of catalyst were placed in the reactor. Results are summarized in Table 1.

CATALYST EXAMPLE 9

27.42 g V₂O₅ powder was added to a solution consisting of 100 ml 30% H₂O₂ in 900 ml of water in a 2 liter beaker. After the reaction of the V₂O₅ powder was complete, 61.22 g of Sb₂O₃ and 2.40 g of fumed TiO₂ (Degussa P-25) powder were added. The beaker was covered with a watch glass and the mixture was stirred and heated for about 3 hours. 84.50 g of 10.7% SnO₂ sol (Nalco Chemical Co.) was added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–3:5 mesh. A portion of this catalyst was calcined for 3 hours at 810° C. then at 650° C. for an additional 3 hours.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to ammoxidize propane using a ⅛ inch O.D. titanium metal fixed bed reactor equipped with a preheat leg and immersed in a temperature controlled molten salt bath. 7.50 g of catalyst were placed in the reactor. Results are summarized in Table 1.

Comparative Catalyst Example D 27.42 g V₂O₅ powder was added to a solution consisting of 100 ml 30% H₂O₂ in 900 ml of water in a 2 liter beaker. After the reaction of the V₂O₂ powder was complete, 61.22 g of Sb₂O₃ and 2.40 g of fumed TiO₂ (Degussa P-25) powder were added. The beaker was covered with a watch glass and the mixture was stirred and heated for about 3 hours. 84.50 g of 10.7% SnO₂ sol (Nalco Chemical Co.) was added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to ammoxidize propane using a ⅛ inch O.D. titanium metal fixed bed reactor equipped with a preheat leg and immersed in a temperature controlled molten salt bath. 7.125 g of catalyst were placed in the reactor. Results are summarized in Table 1.

CATALYST EXAMPLE 10

27.29 g V₂O₂ powder was added to a solution consisting of 100 ml 30% H₂O₂ in 900 ml of water in a 2 liter beaker. After the reaction of the V₂O₅ powder was complete, 56.85 g of Sb₂O₃ was added. The beaker was covered with a watch glass and the mixture was stirred and heated for about 3 hours. 84.51 g of 10.7% SnO₂ sol (Nalco Chemical Co.) and, 2.40 g of TiO₂ powder, were added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C. then at 650° C. for an additional 3 hours.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to ammoxidize propane using a 0.5 inch O.D. titanium metal fixed bed reactor equipped with a preheat leg and immersed in a temperature controlled fluidized sand bath. 8.151 g of catalyst were mixed with 4 ml of quartz chips (20–35 mesh particle size) and placed in the reactor. Results are summarized in Table 1.

CATALYST EXAMPLE 11

27.42 g $V_2O_5$ powder was added to a solution consisting of 100 ml 30% $H_2O_2$ in 900 ml of water in a 2 liter beaker. After the reaction of the $V_2O_2$ powder was complete, 61.22 g of $Sb_2O_3$ was added. Then 0.38 g of $LiOH.H_2O$ was added. The beaker was covered with a watch glass and the mixture was stirred and heated for about 3 hours. 84.50 g of 10.7% $SnO_2$ sol (Nalco Chemical Co.) and 2.40 g of $TiO_2$ powder were added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C. then at 650° C. for an additional 3 hours.

The calcined catalyst was then contacted with isobutanol using about 6.25 ml of isobutanol per gram of catalyst by placing the catalyst in a coarse glass flit funnel, pouring the isobutanol over the catalyst, stiffing the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to atomoxidize propane using a ⅛ inch O.D. titanium metal fixed bed reactor equipped with a preheat leg and immersed in a temperature controlled molten salt bath. Results are shown in Table 2, and can be compared to results shown using Comparative Catalyst Example E.

Comparative Catalyst Example E 27.42 g $V_2O_5$ powder was added to a solution consisting of 100 ml 30% $H_2O_2$ in 900 ml of water in a 2 liter beaker. After the reaction of the $V_2O_5$ powder was complete, 61.22 g of $Sb_2O_3$ was added. Then 0.38 g of $LiOH.H_2O$ was added. The beaker was covered with a watch glass and the mixture was stirred and heated for about 3 hours. 84.50 g of 10.7% $SnO_2$ sol (Nalco Chemical Co.) and 2.40 g of $TiO_2$ powder were added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. After the last of the isobutanol had passed through the funnel, the catalyst was heated in an oven at 120° C. to remove the residual isobutanol on the catalyst.

CATALYST EXAMPLE 12

27.42 g $V_2O_2$ powder was added to a solution consisting of 100 ml 30% $H_2O_2$ in 900 ml of water in a 2 liter beaker. After the reaction of the $V_2O_2$ powder was complete, 61.22 g of $Sb_2O_3$ was added. Then 0.13 g of $LiOH.H_2O$ was added. The beaker was covered with a watch glass and the mixture was stirred and heated for about 3 hours. 84.50 g of 10.7% $SnO_2$ sol (Nalco Chemical Co.) and 2.40 g of $TiO_2$ powder were added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C. then at 650° C. for an additional 3 hours.

The calcined catalyst was then contacted with isobutanol using about 6.25 ml of isobutanol per gram of catalyst by placing the catalyst in a coarse glass flit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to ammoxidize propane using a ⅛ inch O.D. titanium metal fixed bed reactor equipped with a preheat leg and immersed in a temperature controlled molten salt bath. Results are shown in Table 2, and can be compared to results shown using Comparative Catalyst Example F.

Comparative Catalyst Example F 27.42 g $V_2O_5$ powder was added to a solution consisting of 100 ml 30% $H_2O_2$ in 900 ml of water in a 2 liter beaker. After the reaction of the $V_2O_5$ powder was complete, 61.22 g of $Sb_2O_3$ was added. Then 0.13 g of $LiOH—H_2O$ was added. The beaker was covered with a watch glass and the mixture was stiffed and heated for about 3 hours. 84.50 g of 10.7% $SnO_2$ sol (Nalco Chemical Co.) and 2.40 g of $TiO_2$ powder were added to the foregoing dispersion. The mixture was stiffed in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of four times. After the last of the isobutanol had passed through the funnel, the catalyst was heated in an oven at 120° C. to remove the residual isobutanol on the catalyst.

CATALYST EXAMPLE 13

21.95 g $V_2O_5$ powder was added to a solution consisting of 100 ml 30% $H_2O_2$ in 900 ml of water in a 2 liter beaker. After the reaction of the $V_2O_5$ powder was complete, 49.01 g of $Sb_2O_3$ was added. The beaker was covered with a watch glass and the mixture was stirred and heated for about 3 hours. 71.67 g of 10.7% $SnO_2$ sol (Nalco Chemical Co.) and 1.92 g of $TiO_2$ powder were added to the foregoing dispersion. 66.7 g silica sol (Nissan N-30); 30 weight percent silica, were then added. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C. then at 650° C. for an additional 3 hours.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to atomoxidize propane using a ⅛ inch O.D. titanium metal fixed bed reactor equipped with a preheat leg and immersed in a temperature controlled molten salt bath. 3.0 g of catalyst were placed in the reactor. The results shown in Table 2 can be compared to the results using Comparative Catalyst Example G.

Comparative Catalyst Example G 21.95 g $V_2O_5$ powder was added to a solution consisting of 100 ml 30% $H_2O_2$ in 900 ml of water in a 2 liter beaker. After the reaction of the $V_2O_5$ powder was complete, 49.01 g of $Sb_2O_3$ was added. The beaker was covered with a watch glass and the mixture was stirred and heated for about 3 hours. 71.67 g of 10.7% $SnO_2$ sol (Nalco Chemical Co.) and 1.92 g of $TiO_2$ powder were added to the foregoing dispersion. 66.7 g silica sol (Nissan N-30); 30 weight percent silica, were then added. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C.

The calcined catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to ammoxidize propane using a ⅛ inch O.D. titanium metal fixed bed reactor equipped with a preheat leg and immersed in a temperature controlled molten salt bath. 3.0 g of catalyst were placed in the reactor. Results are summarized in Table 2.

CATALYST EXAMPLE 14

27.42 g $V_2O_5$ powder was added to a solution consisting of 100 ml 30% $H_2O_2$ in 900 ml of water in a 2 liter beaker. After the reaction of the $V_2O_5$ powder was complete, 61.22 g of $Sb_2O_3$ was added. The beaker was covered with a watch glass and the mixture was stirred and heated for about 3 hours. 43.89 g of 20.6% $SnO_2$ sol (Nalco Chemical Co.) and 2.40 g of $TiO_2$ powder were added to the foregoing dispersion. The mixture was stirred in an uncovered beaker with heating in order to reduce the volume by evaporation of water. When the mixture could no longer be stirred, it was dried in an oven at 120° C. Thereafter it was calcined for 8 hours at 650° C., cooled and then crushed and sieved to 20–35 mesh. A portion of this catalyst was calcined for 3 hours at 810° C. then heat treated at 650° C. for an additional 8 hours.

The heat treated catalyst was then contacted with isobutanol using about 6.25 ml of isobutanol per gram of catalyst by placing the catalyst in a coarse glass frit funnel, pouring the isobutanol over the catalyst, stirring the catalyst in the isobutanol in order to spread the catalyst evenly over the bottom of the funnel, then allowing the isobutanol to pass through the funnel without suction. This was done a total of three times. After the last of the isobutanol had passed through the funnel, the catalyst was heated in an oven at 120° C. to remove the residual isobutanol on the catalyst.

The catalyst was used to ammoxidize propane using a ⅛ inch, O.D. titanium metal fixed bed reactor equipped with a preheat leg and immersed in a temperature controlled molten salt bath. 5 g of catalyst were placed in the reactor. Results are summarized in Table 2.

TABLE 1

(See Table 2 for footnotes)

| Example No. (3) | Catalyst Example No. | Mole Ratios | Temp. °C. | CT Secs (4) | Percent Propane Conversion | Propane: Mole % Conversion to (2) AN | % Selectivity (1) AN |
|---|---|---|---|---|---|---|---|
| | | $C_3/NH_3/O_2/H_2O$ (6) | | | | | |
| 15 | 1 | 5/1.1/2.8/1 | 460 | 2.5 | 15.6 | 9.6 | 61.7 |
| 16 (5) | A (5) | " | " | 1.7 | 14.7 | 9.0 | 60.9 |
| 17 | 2 | " | " | 3.2 | 13.8 | 9.0 | 65.1 |
| 18 | 3 | " | " | 3.2 | 14.6 | 9.6 | 65.6 |

TABLE 1-continued (See Table 2 for footnotes)

| Example No. (3) | Catalyst Example No. | Mole Ratios | Temp. °C. | CT Secs (4) | Percent Propane Conversion | Propane: Mole % Conversion to (2) AN | % Selectivity (1) AN |
|---|---|---|---|---|---|---|---|
| 19 | 4 | " | " | 3.7 | 15.1 | 9.5 | 62.7 |
| 20 (5) | B (5) | " | " | 1.7 | 14.9 | 9.1 | 61.3 |
| 21 | 5 | " | " | 3.6 | 14.5 | 9.3 | 64.2 |
| 22 (5) | C (5) | " | " | 0.9 | 15.5 | 8.3 | 53.8 |
| 23 | 6 | " | " | 1.2 | 15.2 | 8.9 | 58.7 |
|  |  | +e,uns C$_3$/NH$_3$/O$_2$/N$_2$/H$_2$O+ee |  |  |  |  |  |
| 24 | 7 | 3/1.29/3.01/10.34/2.0 | 480 | 4.4 | 30.6 | 18.2 | 59.5 |
| 25 | 8 | " | " | 4.9 | 31.4 | 18.3 | 58.1 |
| 26 | 9 | " | " | 3.7 | 30.6 | 17.6 | 57.5 |
| 27 (5) | D (5) | " | " | 2.2 | 29.7 | 16.2 | 54.7 |
|  |  | C$_3$/NH$_3$O$_2$/N$_2$ |  |  |  |  |  |
| 28 | 10 | 5/1.33/3.31/10.81 | 460 | 2.9 | 17.6 | 11.6 | 66.3 |
| 29 | 10 | 3/1.49/3.16112.39 | " | 7.5 | 37.4 | 18.0 | 57.4 |

TABLE 2

| Example No. (3) | Catalyst Example No. | Mole Ratios C$_3$/NH$_3$/O$_2$/H$_2$O (6) | Temp. °C. | CT Secs (4) | Percent Propane Conversion | Propane: Mole % Conversion to (2) AN | % Selectivity (1) AN |
|---|---|---|---|---|---|---|---|
| 30 | 11 | 5/1/2.8/1 | 460 | 2.0 | 15.4 | 9.7 | 62.8 |
| 31 (5) | E (5) | " | " | 0.7 | 14.9 | 8.9 | 59.8 |
| 32 | 12 | " | " | 2.1 | 14.5 | 9.1 | 62.7 |
| 33 (5) | F (5) | " | " | 1.0 | 15.4 | 9.2 | 59.7 |
| 34 | 13 | " | " | 4.1 | 17.0 | 10.1 | 59.6 |
| 35 (5) | G (5) | " | " | 1.9 | 14.3 | 8.3 | 57.7 |
| 36 | 14 | " | " | 4.0 | 14.9 | 9.5 | 63.5 |

(1) Selectivity based on propane
(2) AN is Acrylonitrile
(3) Propane Ammoxidation runs
(4) Contact Time, Seconds
(5) Control Example
(6) C$_3$ is Propane While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for the manufacture of acrylonitrile under standard ammoxidation conditions from a hydrocarbon selected from propylene, propane and mixtures thereof comprising reacting the hydrocarbon with NH$_3$ and O$_2$ in the presence of a catalyst made by the following steps comprising:

calcining a catalyst mixture at a temperature above 750° C.; and heat treating the calcined catalyst mixture at an effective temperature which is at least 500° C. and at least 50° C. below said calcining temperature;

wherein said catalyst mixture has the elements and relative amounts indicated by the formula $V_vSb_mA_aD_dO_x$ wherein A when present is Sn and/or Ti; D when present is one or more of Li, Mg, Na, Ca, Sr, Ba, Co, Fe, Cr, Ga, Ni, Zn, Ge, Nb, Zr, Mo, W, Cu, Te, Ta, Se, Bi, Ce, In, As, B, Al and Mn; and all of the elements of said formula, except oxygen, are present at cations, and v is 1, m is 0.5–10, a is up to 10, d is up to 10, and x is determined by the oxidation state of the cations present.

2. The process of claim 1 wherein v+m+a>0.5d.
3. The process of claim 1 wherein a is ≦v+m.
4. The process of claim 2 wherein a is ≦v+m.
5. The process of claim 1 wherein the hydrocarbon is propane.
6. The process of claim 5 wherein v+m+a>0.5d.
7. The process of claim 6 wherein a is ≦v+m.
8. The process of claim 5 wherein a is ≦v+m.
9. The process of claim 1 wherein the calcination temperature is in the range of over 750° C. to up to 1050° C.
10. The process of claim 2 wherein the calcination temperature is in the range of over 750° C. to up to 1050° C.
11. The process of claim 4 wherein the calcination temperature is in the range of over 750° C. to up to 1050° C.

* * * * *